US010196415B2

(12) United States Patent
Yang et al.

(10) Patent No.: US 10,196,415 B2
(45) Date of Patent: Feb. 5, 2019

(54) METHOD OF MANUFACTURING D-GALACTOSE FOR USE OF THE PRODUCTION OF D-TAGATOSE FROM WHEY PERMEATE OR DRIED WHEY PERMEATE

(71) Applicant: CJ CHEILJEDANG CORPORATION, Seoul (KR)

(72) Inventors: Sung Jae Yang, Gwangmyeong-si (KR); Min Hae Kim, Incheon (KR); Taek Beom Kim, Seoul (KR); Young Mi Lee, Bucheon-si (KR); Seong Bo Kim, Seoul (KR); Seung Won Park, Yongin-si (KR)

(73) Assignee: CJ CHEILJEDANG CORPORATION, Seoul (KR)

( * ) Notice: Subject to any disclaimer, the term of this patent is extended or adjusted under 35 U.S.C. 154(b) by 193 days.

(21) Appl. No.: 14/386,771

(22) PCT Filed: May 23, 2013

(86) PCT No.: PCT/KR2013/004544
§ 371 (c)(1),
(2) Date: Sep. 19, 2014

(87) PCT Pub. No.: WO2014/189163
PCT Pub. Date: Nov. 27, 2014

(65) Prior Publication Data
US 2016/0152652 A1 Jun. 2, 2016

(51) Int. Cl.
*C07H 3/02* (2006.01)
*C12P 19/02* (2006.01)
*C07H 1/08* (2006.01)
*B01D 61/42* (2006.01)

(52) U.S. Cl.
CPC .......... *C07H 3/02* (2013.01); *B01D 61/422* (2013.01); *C07H 1/08* (2013.01); *C12P 19/02* (2013.01)

(58) Field of Classification Search
CPC .......... B01D 61/422; C07H 1/08; C07H 3/02; C12P 19/02
See application file for complete search history.

(56) References Cited

U.S. PATENT DOCUMENTS

| 1,533,030 | A | * | 4/1925 | Sauer | C13B 20/123 |
| | | | | | 127/55 |
| 4,202,909 | A | * | 5/1980 | Pederson, Jr. | C13K 5/00 |
| | | | | | 426/239 |
| 5,002,612 | A | | 3/1991 | Beadle et al. | |
| 5,078,796 | A | * | 1/1992 | Beadle | C13K 13/00 |
| | | | | | 127/36 |
| 6,057,135 | A | * | 5/2000 | Ibrahim | C12N 9/90 |
| | | | | | 426/658 |
| 6,991,923 | B2 | * | 1/2006 | Bertelsen | C12N 9/90 |
| | | | | | 435/105 |
| 2004/0132989 | A1 | | 7/2004 | Lifran et al. | |
| 2007/0134373 | A1 | | 6/2007 | Cipoletti et al. | |
| 2011/0275128 | A1 | | 11/2011 | Lee | |

FOREIGN PATENT DOCUMENTS

| CN | 1985624 A | 6/2007 |
| CN | 101925609 A | 12/2010 |
| KR | 10-1999-0038067 A | 6/1999 |
| KR | 10-0190671 B1 | 6/1999 |
| RU | 2409965 C2 | 1/2011 |
| WO | 0250089 A1 | 6/2002 |
| WO | 2005/039299 A2 | 5/2005 |

OTHER PUBLICATIONS

Smith, Karen "Dried Dairy Ingredients: Types of Milk, Whey and Permeate; Dried Dairy Ingredients; Dairy Ingredients from Milk; Dairy Ingredients from Whey" Wisconsin Center for Dairy Research, May 15, 2008, pp. 1-59.*
L. A. Dohan et al., "Lactose hydrolysis by immobilized lactase: Semi-industrial experience", Enzyme Engineering, 1980, pp. 279-293.
Zhao Li, "Study on Extract Lactose from Whey by Crystallization and Membrane Filtration Process", Jun. 15, 2010, pp. 15-19.
Literature Food Science Journal, 2010, pp. 227-229.
Office Action dated Jul. 9, 2015 of corresponding Chinese Patent Application No. 201380023775.4—9 pages.
Wanarska et al., "A method for the production of D-tagatose using a recombinant Pichia pastoris strain secreting β-D-galactosidase from Arthrobacter chlorophenolicus and a recombinant L-arabinose isomerase from *Arthrobacter* sp. 22c", Microbial Cell Factories, 2012, vol. 11, No. 113, pp. 1-15.
Examiner's Report dated Jun. 17, 2015 of corresponding Australian Patent Application No. 2013378056—7 pages.
Search report and Written Opinion dated Feb. 24, 2014 of PCT/KR2013/004544 which is the parent application—8 pages.
E.J. Guy, Removal of Residual Protein from Cheese Whey Permeates by Bentonite 1979, J. Darry Sci, vol. 62, No. 5; pp. 776-780—5 pages.

(Continued)

*Primary Examiner* — Aaron J Kosar
(74) *Attorney, Agent, or Firm* — Knobbe Martens Olson & Bear LLP

(57) ABSTRACT

A method for producing D-galactose from a dissolved solution of dried whey permeate or a liquid whey permeate is disclosed. The method comprises: removing non-sugar insoluble materials from the dissolved solution of dried whey permeate or the liquid whey permeate; removing protein from the dissolved solution of dried whey permeate or the liquid whey permeate from which non-sugar solid precipitates are removed; and removing ash, salts or both from the dissolved solution of dried whey permeate or the liquid whey permeate from which the proteins are removed. Another method for producing D-tagatose is disclosed. The other method comprises isomerizing D-galactose produced by the foregoing method.

13 Claims, 6 Drawing Sheets

(56) References Cited

OTHER PUBLICATIONS

Extended European Search Report dated Dec. 19, 2016 of corresponding European Patent Application No. 13882627.6—14 pages.
Partial European Search Report issued in European Application No. 13882627.6, dated Sep. 23, 2016, in 7 pages.
Joint FAO/WHO Expert Committee on Food Additives Sixty-third meeting (Food additives), Geneva, Jun. 8-17, 2004, in 12 pages.

* cited by examiner

Supernatant after centrifugation: Supernatant / Undissolved precipitate $$\text{Removal rate of undissolved materials (\%, based on dried weight)} = \frac{2.694\text{g of dried undissolved precipitate}}{60\text{g of DWP}} \times 100 = 4.49$$

DWP dissolved solution after pretreatment centrifugation[a]

DWP dissolved solution after pretreatment centrifugation, removal of protein with activated carbon[b]

a 20%(w/v) DWP pretreatment(pH 6.8, 70°C, 30min)
  →Centrifugation
b 20%(w/v) DWP pretreatment(pH 6.8, 70°C, 30min)
  →Centrifuged solution
  →2g/LA Activated carbon (70°C, 6hr)
  →Centrifugation

METHOD OF MANUFACTURING D-GALACTOSE FOR USE OF THE PRODUCTION OF D-TAGATOSE FROM WHEY PERMEATE OR DRIED WHEY PERMEATE

TECHNICAL FIELD

The present invention relates to a method for producing D-galactose for use in production of D-tagatose from liquid whey permeate or dried whey permeate (hereinafter referred to as "DWP"). More particularly, the present invention relates to a method for mass production of D-galactose from inexpensive raw materials by removing impurities such as protein, ash (including salts), other non-sugar insoluble materials, and the like from dried whey permeate or liquid whey permeate occurring in the process of producing whey protein isolates from whey. The present invention also relates to a method for mass production of D-tagatose from D-galactose obtained by the present invention.

BACKGROUND ART

There has been an explosion in demand for low-calorie and functional sweeteners capable of preventing excessive caloric intake, obesity and tooth decay owing to sugar consumption.

D-tagatose is an ideal low-calorie sweetener as an alternative sugar that can satisfy such consumer demand. D-tagatose has about 90% the sweetness of sucrose, thus being substantially identical thereto, but has 30% the calories of sucrose.

Further, it is known that D-tagatose, a stereoisomer of D-galactose, has low metabolic speed and absorption rate in the body, and thus can be used as a low-calorie sweetener without side effects (see: JECFA Sixty-third meeting, Geneva, 8-17 Jun. 2004—Food Additives).

Only 20% of D-tagatose is absorbed in the small intestine and the remaining 80% thereof is moved to the large intestine where intestinal microbes live and selectively accelerates the production of *lactobacillus*, thereby producing short chain fatty acids. Particularly, D-tagatose has a prebiotic characteristic of producing butyrate, which is known to help prevent colon cancer, in large quantities (up to 50% of the total short chain fatty acids). Further, D-tagatose is a natural sugar having a low-calorie value of 1.5 kcal/g and has attained GRAS (Generally Recognized As Safe) status under the U.S. Food and Drug Administration (FDA), thereby allowing use as a functional sweetener in foods, beverages, health foods, diet additives, and the like.

However, D-tagatose is not often found in nature and is a rare sugar present only in trace amounts in dairy products and some plants. In order to use D-tagatose as a low-calorie and functional sweetener, it is essential to develop a method for mass production of D-tagatose from inexpensive raw materials.

U.S. Pat. Nos. 5,002,612 and 5,078,796 disclose a method for producing D-tagatose by hydrolyzing lactose or lactose-containing materials by adding lactase to a mixture of D-galactose and D-glucose, removing optional D-glucose from the mixture, and then chemically isomerizing D-galactose into D-tagatose.

Thus, an essential intermediate in the enzymatic production of D-tagatose is D-galactose. Currently, supply of D-galactose developed up to now is restricted to hydrolysis of lactose However, lactose prices vary due to unpredictable factors, such as amount of raw milk produced according to weather, demand for powder milk, changes in lactose consumption in third world countries, and the like, and exhibit a unique price pattern of repeating fall and rise in price. Such price fluctuations in the raw milk market make stable supply of raw materials for producing D-tagatose difficult.

According to the present invention, it is possible to obtain D-galactose from inexpensive whey permeate or dried whey permeate occurring in the process of producing whey protein isolates and to use D-galactose to produce D-tagatose. Therefore, stable supply of raw materials and price stabilization of D-tagatose can be ensured, thereby creating considerable added value.

SUMMARY

Currently, the production of D-galactose, which is a raw material for the production of D-tagatose through enzymatic processes, depends on lactose. However, unstable supply of lactose and high price of lactose directly affect production cost of D-tagatose. Accordingly, more stable supply of inexpensive raw materials, i.e., lactose and D-galactose, is a prerequisite for mass production of D-tagatose. As a result of extensive studies to develop inexpensive materials as raw materials for producing D-tagatose, the present inventors have developed a technology capable of economically utilizing whey permeate or dried whey permeate occurring as by-products in production of whey protein isolates, industrial use of which is not relatively high.

Since whey permeate or dried whey permeate contains proteins, ash (including salts), and other impurities, in addition to carbohydrates (lactose), there is a need for a method for economically and effectively isolating lactose from other components in order to use whey permeate or dried whey permeate as a raw material for D-tagatose production.

In the present invention, a dissolved solution of dried whey permeate or a liquid whey permeate is subjected to physical and chemical pretreatment, such as pH adjustment, heat treatment, and the like, to remove non-sugar insoluble materials by inducing solidification without changing sugar content or forming by-products. Further, in order to achieve efficient and economic removal of proteins from the dissolved solution of dried whey permeate or the liquid whey permeate, from which the insoluble precipitates are removed, activated carbon treatment is used instead of a conventional adsorption method or ion chromatography entailing relatively high cost.

Further, the dissolved solution of dried whey permeate or the liquid whey permeate from which solid precipitates and proteins are removed is subjected to electrodialysis to remove salts, ash or both of salts and ash contained the dissolved solution. Thus, the method according to the present invention can minimize contamination of a membrane employed in electrodialysis while improving desalting efficiency through pretreatment of removing the solid precipitates and proteins.

The present invention provides an effect of overcoming dependency on the provision of purified lactose and/or crystalline lactose, which are used as raw materials for D-tagatose in the art, and can directly or indirectly reduce costs for producing D-tagatose by providing a method for effectively and economically removing protein, ash (including salts), and other solid precipitates, excluding lactose in whey permeate or dried whey permeate, which is a by-product in production of whey protein isolates.

The present invention also provides a technology capable of economically utilizing whey permeate or dried whey permeate produced as by-products in production of whey protein isolates, industrial use of which is not relatively high.

MODE FOR INVENTION

Figure 1:
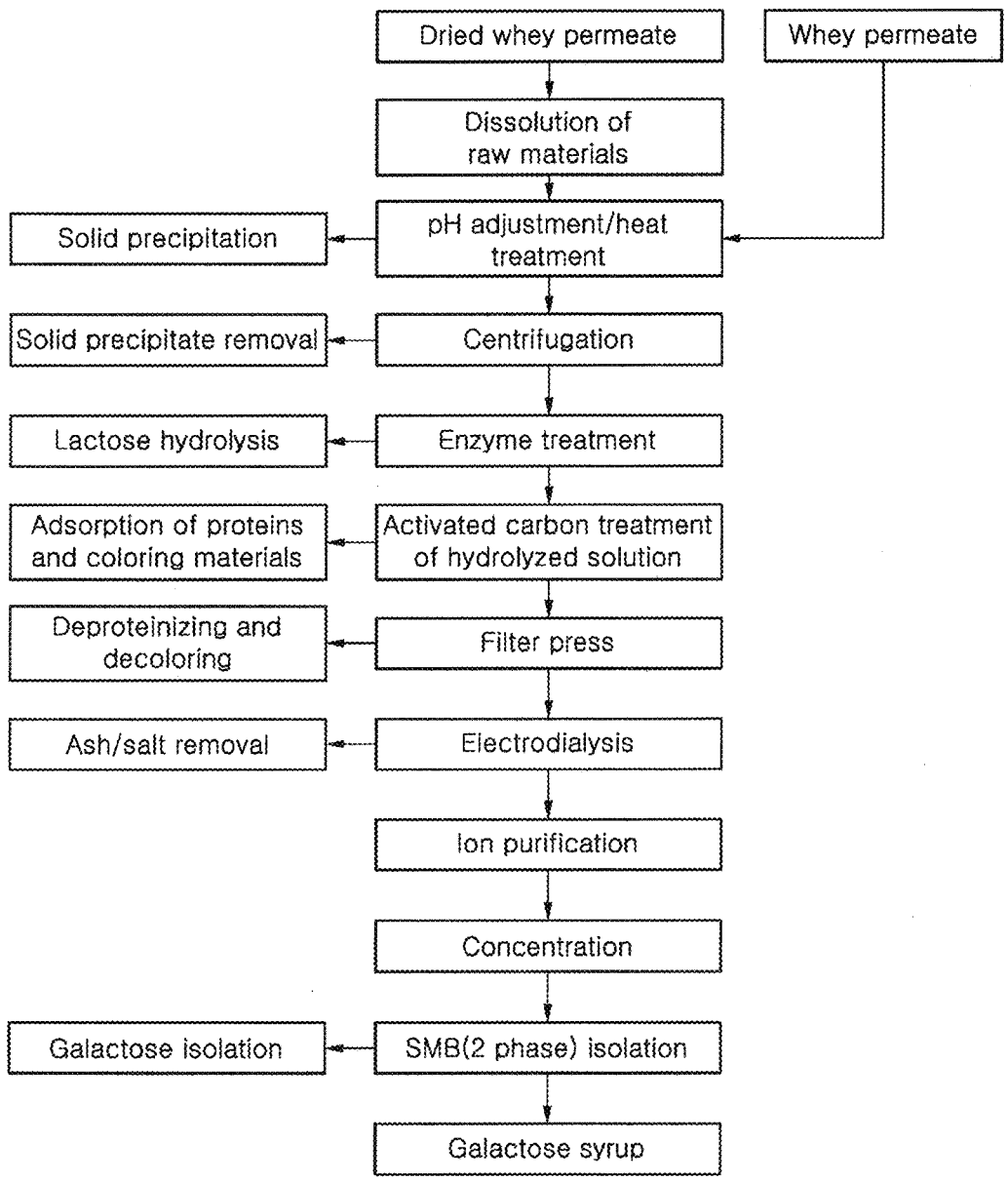
FIG. 1 is a flowchart of an overall process for producing D-galactose according to one aspect of the present invention.

The present invention relates to a method for producing D-galactose from a dissolved solution of dried whey permeate or a liquid whey permeate, which includes: removing solid precipitates from a dissolved solution of dried whey permeate or a liquid whey permeate; removing proteins from the dissolved solution of dried whey permeate or the liquid whey permeate from which solid precipitates are removed; and removing ash, salts or both ash and salts from the dissolved solution of dried whey permeate or the liquid whey permeate from which both solid precipitates and proteins are removed.

The method for producing D-galactose according to the present invention uses, as raw materials, both liquid whey permeate and dried whey permeate produced as by-products in production of whey protein isolates. When using liquid whey permeate, the process of removing solid precipitates may be performed without separate treatment. When using dried whey permeate as raw materials, whey permeate may be dissolved in water as a solvent to prepare a dissolved solution of dried whey permeate, and solid precipitates may be removed from the dissolved solution.

As used herein, the term "whey protein isolates" means whey proteins separated and collected by passing whey as a raw material through filter membranes. As used herein, the term "liquid whey permeate" means permeates occurring as by-products during the process of producing "whey protein isolates".

As used herein, the term "dried whey permeate" means dried whey permeate obtained by concentrating and drying liquid whey permeate.

The process of removing solid precipitates may be performed by forming the solid precipitates from the dissolved solution of dried whey permeate or the liquid whey permeate through heat treatment at 40° C. to 90° C., adjusting the dissolved solution to a pH of 3 to 9, or by both treatments, and then separating the solid precipitates by a typical method such as centrifugation and the like. The procedures of heat treatment at 40 to 90° C. and adjustment to a pH of 3 to 9 provide effects of removing solid components without affecting the content and quality of D-galactose, which is a final product, by precipitating solid components in the dissolved solution of dried whey permeate or the liquid whey permeate without causing changes in sugar content in the dissolved solution of dried whey permeate or the liquid whey permeate and forming by-products. Preferably, heat treatment is carried out at a temperature of 50° C. to 80° C., and pH adjustment is carried out to a pH of 4 to 8.

In the present invention, precipitation of solid and insoluble materials without precipitating lactose accelerates with increasing heat treatment temperature. Further, precipitation of the solid and insoluble materials accelerates with increasing pH. Thus, as heat treatment temperature and pH increase, precipitation of solid and insoluble materials may be accelerated, thereby remarkably increasing solid precipitates. In one embodiment, the process of removing solid precipitates is performed by increasing the heat treatment temperature to 60° C. to 80° C. and adjusting the dissolved solution to a pH of 5 to 8.

In the method for producing D-galactose according to the invention, it is possible to remove proteins from the dissolved solution of dried whey permeate or the liquid whey permeate from which the solid precipitates are removed. The process of removing proteins has an advantage in that proteins can be removed using activated carbon without using pre-adsorption or ion chromatography entailing high cost.

In the present invention, the process of removing proteins through activated carbon treatment may include: treating the dissolved solution of dried whey permeate or the liquid whey permeate, from which the solid precipitates have been removed, with activated carbon, and reacting the resultant at 20° C. to 90° C. for 10 minutes to 9 hours. The activated carbon is preferably activated carbon powder, for example, activated carbons A to F, without being limited thereto. In the present invention, activated carbon A is DARCOKB-B produced by Norit Inc., activated carbon B is NORITCGSP produced by Norit Inc., activated carbon C is NORITCASP produced by Norit Inc., activated carbon D is NORITCA1 produced by Norit Inc., activated carbon E is A51 produced by Norit Inc., and activated carbon F is Norit SX plus produced by Norit Inc. More preferably, activated carbon A or B is useful in terms of protein removal efficiency.

The activated carbon treatment is preferably performed at 50° C. to 80° C. for about 3 to 8 hours, more preferably at 55° C. to 75° C. for about 4 to 7 hours.

Protein removal efficiency can be accelerated with increasing treatment time and temperature.

The protein removal method using the activated carbon in the present invention result in further decolorization.

The method for producing D-galactose according to the present invention may further include removing ash, salts or both from the dissolved solution of dried whey permeate or the liquid whey permeate from which proteins are removed. The removal of ash, salts or both may be performed by electrodialysis. In the present invention, since the solid precipitates and proteins are removed prior to the electrodialysis, contamination of an electrodialysis membrane can be minimized, thereby prolonging lifespan of the electrodialysis membrane while improving salt removal efficiency.

The method according to the present invention may further include adding lactase to the dissolved solution of dried permeate or the liquid whey permeate before or after any one of the solid precipitate removal, protein removal, and ash and/or salts removal. Preferably, the process of adding lactase is performed after the solid precipitate removal and before the protein removal.

As the lactase, any known enzymes may be employed without limitation. Examples of lactase may include Maxilact LX 5000, Maxilact LG 5000 produced by DSM Inc.

The enzyme can be added at a concentration of 0.01 w/v % to 5 w/v %. With the use of enzymes, hydrolysis may be performed using a fermenter at 35° C. to 39° C.

The method according to the present invention may further include ion purification, concentration and chromatography separation procedures after the salt and/or ash removal. Specifically, in order to separate, purify and harvest D-galactose using SMB (Simulated Moving Bed) chromatography, ion purification and concentration may be performed. Prior to SMB chromatography separation and purification, cation and anion purification chromatography typically used in ion removal, or a concentration process conventionally used in the art may be performed. Another embodiment of the present invention relates to a method for producing D-tagatose including isomerizing D-galactose produced by the aforementioned method to obtain D-tagatose.

The present invention will now be described in more detail with reference to the following examples. It should be understood that these examples are provided for illustration only and are not to be in any way construed as limiting the present invention. A description of details apparent to those skilled in the art will be omitted herein.

EXAMPLES

Example 1: Component Analysis of Dried Whey Permeate (DWP)

The contents and sorts of impurities in a raw material were identified by component analysis of dried whey permeate, which is a by-product in production of whey protein isolates from whey. Analysis results of the components in the dried whey permeate are shown in Table 1. The dried whey permeate contained lactose in an amount of greater than 80% and included proteins, fat, various kinds of inorganic salts, and heavy metals, in addition to sugar component. In order to remove remaining components except for the sugar component, the dried whey permeate were subjected to physical and chemical pre-treatment.

TABLE 1

| Total components | |
| --- | --- |
| Total carbohydrate | 86.9% |
| Total protein | 3.6% |
| Total fatty acid | 0.2% |
| Moisture | — |
| Ash | 9.5% |
| Salt | |
| Calcium ion | 742.99 mg/100 g |
| Magnesium ion | 135.54 mg/100 g |
| Sodium ion | 562.99 mg/100 g |
| Potassium ion | 2231.12 mg/100 g |
| Iron | 0.22 mg/100 g |
| Phosphorus | 113.1 mg/100 g |
| Zinc | 0.05 mg/100 g |
| Copper | 0.03 mg/100 g |
| Manganese | 0.01 mg/100 g |
| Selenium | 36.23 ug/100 g |
| Sugar | |
| Lactose | 85.1% |
| D-galactose | 1.6% |

[Based on % TS]

Example 2: Pre-Treatment Process to Remove Insoluble Materials in Dried Whey Permeate (DWP)

4 g of dried whey permeate (DWP) produced by Hilmar Inc. was suspended and dissolved in 20 ml of water (~20%, w/v) to prepare a dissolved solution of dried whey permeate. The prepared dissolved solution of DWP was subjected to physical and chemical pre-treatment to induce the precipitation of insoluble solid materials without changing sugar content in DWP and without forming by-products, thereby removing only impurities. In order to evaluate the removal rate of insoluble material precipitates in DWP dissolved solution depending on conditions for heat treatment and pH, the prepared dissolved solution of dried whey permeate was heat treated at 50° C. to 80° C. for one hour. Further, for specimens prepared by changing the pH condition, suspensions were titrated with HCl and NaOH to pH 4.0-8.0, followed by treatment at room temperature (~25° C.) for 1 hour. The resulting supernatants recovered by centrifugation were subjected to analyze the changes of pH (using a pH meter), conductivity (using a conductivity meter), Brix (using a Brix meter), lactose content (using HPLC) and protein content (using Bradford protein assay) (Table 2).

TABLE 2

| | Temperature (° C.) - reaction for 60 minutes[a] | | | | pH (pH adjust with use of HCl/NaOH) - reaction at room temperature for 60 minutes | | | | |
| --- | --- | --- | --- | --- | --- | --- | --- | --- | --- |
| Analysis | 50 | 60 | 70 | 80 | 4.0 | 5.0 | 6.0 | 7.0 | 8.0 |
| pH | 5.745 (5.778)[b] | 5.712 (5.763) | 5.6 (5.796) | 5.449 (5.781) | 3.9 | 5.0 | 6.1 | 7.0 | 7.7 |
| Conductivity (μs/cm) | 11980 (12040) | 11670 (12130) | 11630 (12220) | 11850 (12200) | 14030 | 12500 | 11720 | 12390 | 12910 |
| Brix (%) | 16.82 (16.82) | 16.75 (16.49) | 16.65 (16.61) | 16.76 (16.76) | 16.2 | 16.7 | 16.5 | 16.4 | 16.6 |
| Lactose (g/L) | 159.3 (153.1) | 153.7 (156.0) | 154.8 (153.3) | 155.9 (155.5) | 145.8 | 157.5 | 155.4 | 153.1 | 151.5 |
| Protein (g/L) | 0.230 (0.227) | 0.233 (0.227) | 0.229 (0.227) | 0.228 (0.228) | 0.217 | 0.232 | 0.238 | 0.237 | 0.239 |

[a] pH of 20% (w/v) DWP dissolved solution is 5.7.
[b] Numbers in parenthesis mean analysis results of specimens prior to heat treatment.

As shown in Table 2, with changes in heat treatment temperature (50° C. to 80° C.), the reaction showed no change in lactose content, protein content, Brix, pH, and conductivity. With changes in pH from 4 to 8, the reaction did not show substantial changes in lactose content, protein content, Brix, pH and conductivity. These results indicates that the DWP dissolved solution showed no change in sugar content with changes in heat treatment temperature and pH, and neither protein denaturation nor formation of by-products occurred.

Figure 2:
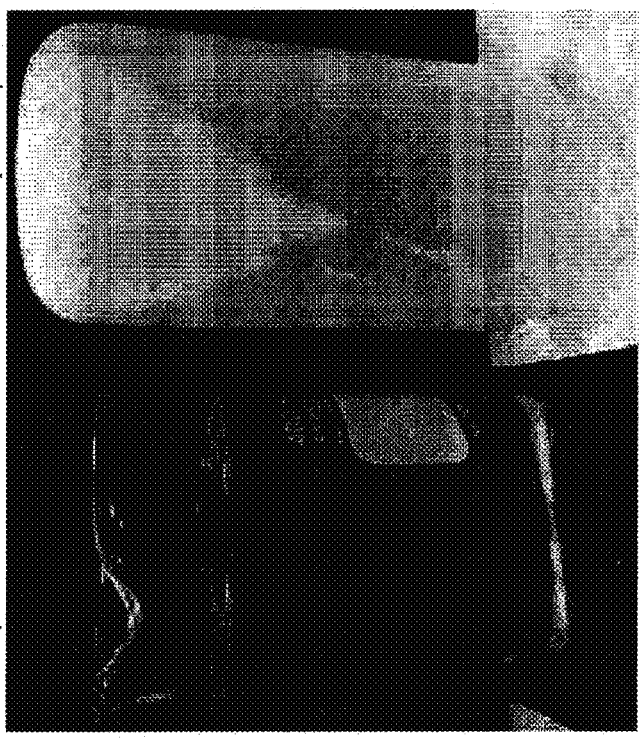
FIG. 2 shows a dried weight of solidified precipitates removed by adjusting a 20% (w/v) dissolved solution of dried whey permeate (DWP) to pH 6.8, subjecting to heat treatment at 70° C. for 30 minutes and then centrifugation.

However, it can be seen that, as heat treatment temperature increases, the degree of precipitation of insoluble solid materials increases without precipitation of proteins and carbohydrates (lactose). Specifically, it was observed that, as the pH of a 20% (w/v) DWP dissolved solution increased, precipitation of insoluble materials was accelerated, and precipitation of solid materials after centrifugation remarkably increased. Considering the enzymatic hydrolysis conditions of 20% (w/v) DWP dissolved solution, the DWP dissolved solution was adjusted to pH 6.8, heat-treated at 70° C. for 30 minutes, and centrifuged. As a result, about 4.5 wt % (weight of dried precipitate/weight of dried whey permeate) of the insoluble materials could be removed without changing sugar content or forming by-products (see FIG. 2).

Example 3: Enzymatic Hydrolysis Process

In order to enzymatically hydrolyze lactose in DWP dissolved solution, The lactase Maxilact LG 5000 (DSM Inc.) was used. Specimens pretreated in Example 2 and Maxilact LG 5000 in a concentration of 1% (w/v) were reacted at 38° C. and 100 rpm using a reactor.

In order to measure the hydrolysis rate of lactose, samples were taken at 0, 10, 24, 31, 48 and 58 hours after enzymatic hydrolysis began. The content of D-glucose and D-galactose produced in each sample was quantitatively analyzed using HPLC (Aminex HPX-87C column, RI detector, 0.2 ml/min flow rate using $H_2O$ as a mobile phase) (Table 3).

TABLE 3

| Reaction condition | Reaction time (hr) | Lactose content (g/L) | D-Glucose (g/L) | D-Galactose (g/L) | Total sugar content (g/L) | Hydrolysis rate (%) |
| --- | --- | --- | --- | --- | --- | --- |
| 20 L DWP dissolved solution (200 g DWP/L water) | 0 | 227.5 | | | 227.5 | |
| | 10 | 28.4 | 97.4 | 78.7 | 204.5 | 77.4 |
| | 24 | 13.1 | 104.6 | 97.8 | 215.5 | 89.0 |
| | 31 | 10.5 | 106.3 | 102.3 | 219.1 | 91.7 |
| | 48 | 7.4 | 108.1 | 107.5 | 223.1 | 94.8 |
| | 58 | 6.9 | 109.6 | 109.8 | 226.3 | 96.5 |

Example 4: Removal of Proteins in Dried Whey Permeate (DWP) Dissolved Solution and Decoloring Procedure In this example, proteins and coloring materials were removed from the DWP dissolved solution through activated carbon treatment. In order to evaluate a possibility of removing proteins after treatment with various activated carbons A to F, DWP was suspended and dissolved in water at a concentration of 20% (w/v), and the resultant was titrated with NaOH to pH 6.8. After heat treatment at about 70° C. for 30 minutes, the supernatant harvested by centrifugation was treated with six sorts of activated carbon powder (2 g of activated carbon powder/20% DWP dissolved solution L). After reacting at room temperature and 50° C. for a predetermined period of time, the resulting material was subjected to centrifugation to harvest a supernatant. The resultant supernatant was quantitatively analyzed to determine protein content change. Results are depicted in FIG. 3.

Figure 3:
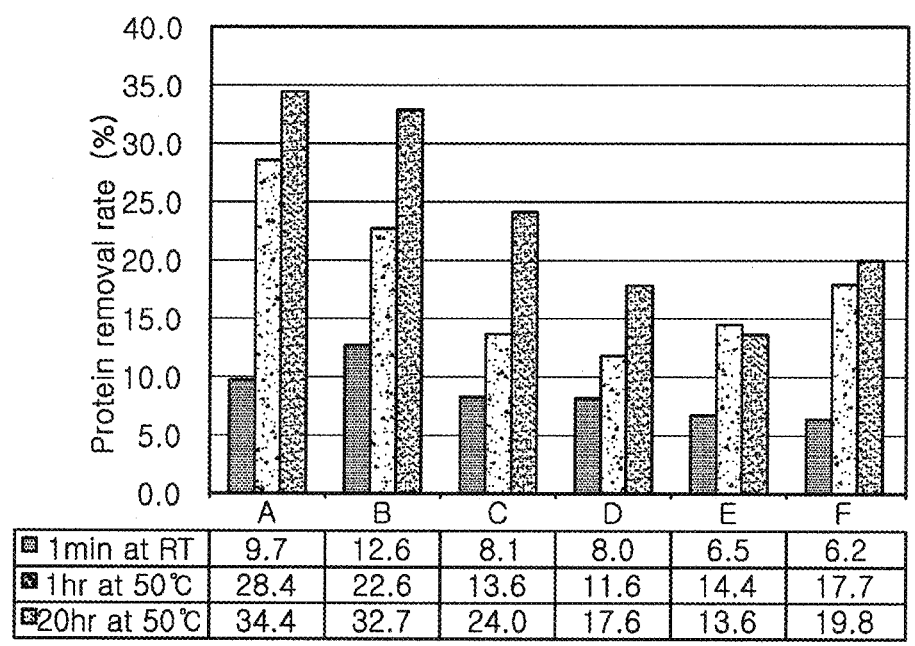
FIG. 3 shows the protein removal yields after treatment with activated carbon powders (A to F), respectively.

As demonstrated in FIG. 3, six sorts of activated carbon A to F exhibited protein removal effect. Thereamong, DARCO KB-B indicated by A and NORIT CGSP indicated by B, both produced by Norit Inc. showed better results than any others in terms of protein removal efficiency. Further, most activated carbons showed a tendency of increasing protein removal yield with increasing reaction time at 50° C.

To optimize the protein removal and decoloring process according to temperature and time conditions after treatment with the activated carbon powders, DWP was suspended and dissolved in water at a concentration of 20% (w/v), and the dissolved solution was titrated with NaOH to pH 6.8. After heat treatment at about 70° C. for 30 minutes, the supernatant harvested by centrifugation was treated with two sorts of activated carbon powders A and B (2 g of activated carbon powder/20% DWP dissolved solution L) and reacted at 40° C. to 70° C. for 0 to 6 hours. The reacted solution was centrifuged to collect a supernatant, which was subjected to quantitative analysis as to protein content change and qualitative analysis as to chromaticity (FIGS. 4 and 5).

Figure 4A:
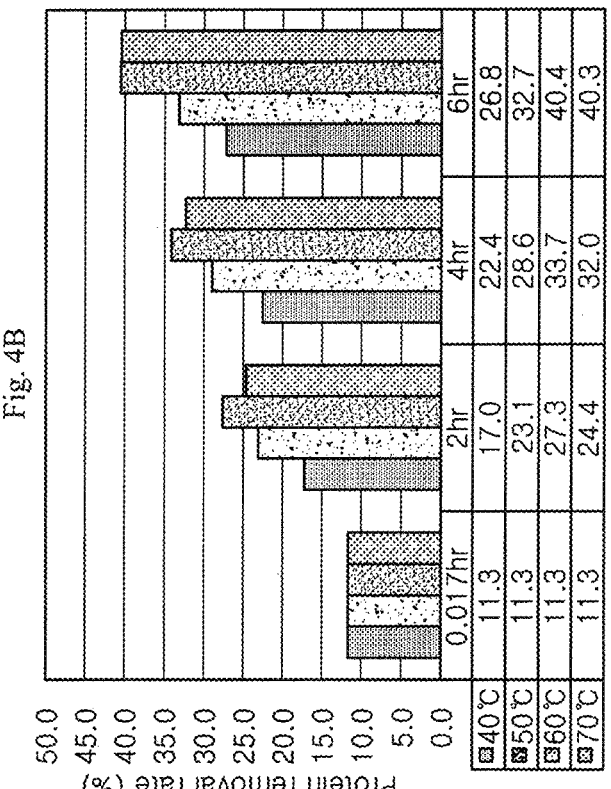
FIG. 4A is a graph depicting results of protein removal yield after treatment with activated carbon A among activated carbon powders of FIG. 3 depending on temperature and time conditions.
Figure 4B:
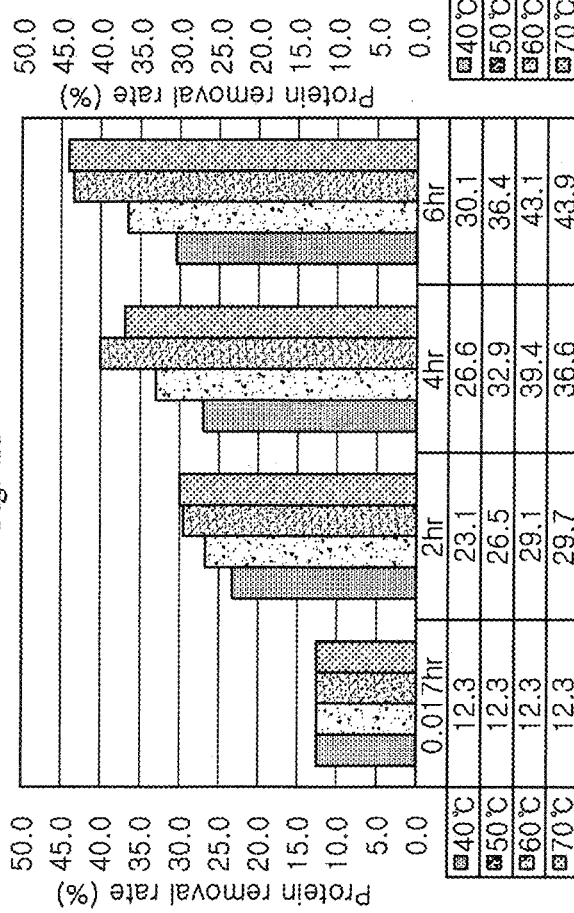
FIG. 4B is a graph depicting results of protein removal yield after treatment with activated carbon B among activated carbon powders of FIG. 3 depending on temperature and time conditions.
Figure 5:
FIG. 5 is a photograph depicting the result of protein removal and decoloring upon treatment with activated carbon A among activated carbon powders of FIG. 3.

As shown in FIG. 4, when the supernatant was treated with activated carbon A (2 g activated carbon powder/20% DWP dissolved solution L) and reacted at 60° C. to 70° C. for about 6 hours, the yield for protein removal was 43% to 44%. When the supernatant was treated with activated carbon B (2 g activated carbon powder/20% DWP dissolved solution L) and reacted at 60° C.-70° C. for about 6 hours, the yield for protein removal was 40%. Further, treatment with activated carbon A exhibited a decoloring effect, as shown in FIG. 5.

Example 5: Desalting Electrodialysis

The lactose hydrolyzed solution prepared through the protein removal process of Example 4 was purified through a desalting electrodialysis device. In order to measure economic feasibility of the desalting electrodialysis process such as desalting rate of ions (salt) and loss rate of organic materials (sugar), energy consumption amount, contamination and the like were examined.

The electrodialysis device used in this example was a 3-compartment type. Detailed descriptions of the electrodialysis device and operation conditions are shown in Table 4.

TABLE 4

| ITEMS | Details |
| --- | --- |
| Equipment | Micro Acilyzer S3 |
| Total efficient membrane area | 0.55 dm²/cell |
| Cartridge | AC-220-550 |
| Electrode | Ti/Pt (Anode) |
| | SUS316L(Cathode) |
| Operation voltage | 9 V-12 V |
| Operation temperature | 23° C.-32° C. |
| Sample liquid | 500 ml |
| Electrode liquid | 5% $Na_2SO_4$ |

The ion exchange membrane used in this example was a commercially available product (CMX, AMX, Astom Corporation, Japan). The characteristics of the ion exchange membrane used in the present invention are shown in Table 5.

TABLE 5

| ITEMS | Cation exchange membrane (CMX) | Anion exchange membrane (AMX) |
|---|---|---|
| Sorts | Strong acidic cation permeable | Strong alkaline anion permeable |
| Characteristic | High mechanical strength (Na-form) | High mechanical strength (Cl-form) |
| Electric resistance ($\Omega$) | 1.8~3.8 | 2.0~3.5 |
| Burat strength | ≥0.40 | ≥0.30 |
| Thickness (mm) | 0.14~0.20 | 0.12~0.15 |

Figure 6:
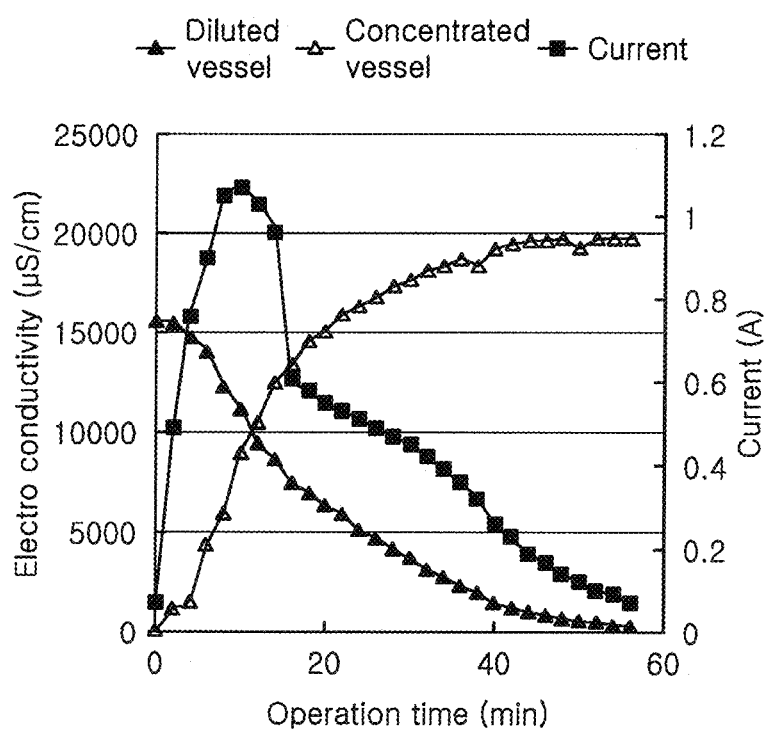
FIG. 6 is a graph depicting electric conductivity and current change depending on changes in electrodialysis operating time.

Electrodialysis was continuously performed without any chemical washing under batch operation conditions, in which power supply to a stack of the electrodialysis device was cut off when conductivity of raw water dropped below a target value, while measuring conductivity of the electrodialysis device in real time [see Table 6 (water quality data for raw water and treated water), FIG. 6].

TABLE 6

| ITEMS | Raw water | Treated water | Removal rate (%) |
|---|---|---|---|
| pH | 6.8 | 6.2 | — |
| Brix (%) | 15.8 | 12.6 | 20.0 |
| Electric conductivity (μs/cm) | 15600 | 300 | 98.10 |
| Protein content (%) | 0.23 | 0.18 | 21.74 |
| Crude fat content (%) | 0.20 | 0.15 | 25.00 |

TABLE 7

| Continuous operation [batch number] | Operation voltage [V] | De-salting time [min] | Sugar Collect rate [%] | Ion removal rate [%] | De-salting rate [LMH] | Energy consumption [Wh] |
|---|---|---|---|---|---|---|
| 1 | 9~12 | 56 | 77 | 98.1 | 9.9 | 6.9 |
| 2 | 9~12 | 50 | 80 | 97.6 | 11.3 | 4.6 |
| 3 | 9~12 | 50 | 79 | 98.0 | 11.2 | 4.3 |
| 4 | 9~12 | 50 | 82 | 97.8 | 11.3 | 4.8 |
| 5 | 9~12 | 50 | 81 | 98.1 | 11.2 | 4.9 |

Table 7 shows the continuous operation of electrodialysis for hydrolyzed lactose solution, from which proteins were removed, without chemical washing.

Ion removal rate=100−{(electric conductivity value of raw water/electric conductivity value of treated water)*100}

As a result, an average desalting rate of ion was 98%, and an average collect rate of sugar was 80%.

Although some embodiments have been described herein, it should be understood by those skilled in the art that these embodiments are given by way of illustration only, and that various modifications, variations, and alterations can be made without departing from the spirit and scope of the invention. Therefore, the scope of the invention should be limited only by the accompanying claims and equivalents thereof.

The invention claimed is:

1. A method for producing a purified D-galactose, comprising:
   (a) providing a whey permeate composition that is a liquid whey permeate or a solution of dried whey permeate;
   (b) subjecting the whey permeate composition to at least one of a heat treatment and pH adjustment to precipitate non-sugar materials in the whey permeate composition;
   (c) removing the precipitated non-sugar materials from the whey permeate composition to provide a liquid composition in which the precipitated non-sugar materials have been removed;
   (d) adding a lactase to the liquid composition thereby hydrolyzing lactose to produce D-galactose in a hydrolysate composition;
   (e) removing proteins by treating the hydrolysate composition with activated carbon for 4 hours to 6 hours at a temperature of 60° C. to 70° C.; and
   (f) removing ash, salts, or both from the deproteinized composition, thereby producing said purified D-galactose.

2. The method according to claim 1, wherein the heat treatment is performed at a temperature between 40° C. and 90° C. and/or wherein the pH adjustment comprises adjusting the pH of the whey permeate composition from 3 to 9.

3. The method according to claim 2, wherein the liquid whey permeate is a byproduct obtained from production of whey protein isolates and comprises lactose, proteins, ash, and salts.

4. The method according to claim 1, wherein removing the proteins using activated carbon decolors the hydrolysate composition.

5. The method according to claim 1, wherein the activated carbon is activated carbon powder.

6. The method according to claim 1, wherein removing the ash, salts, or both is performed by electrodialysis.

7. The method according to claim 1, wherein the hydrolyzing is performed at 35° C. to 39° C. for 50 hours to 60 hours.

8. The method according to claim 1, further comprising:
   performing ion purification, concentration, and chromatography procedures after removing the ash, salts, or both.

9. A method for producing D-tagatose, the method comprising:
   (i) producing purified D-galactose comprising:
      (a) providing a whey permeate composition that is a liquid whey permeate or a solution of dried whey permeate;
      (b) subjecting the whey permeate composition to at least one of a heat treatment and pH adjustment to precipitate non-sugar materials in the whey permeate composition;
      (c) removing the precipitated non-sugar materials from the whey permeate composition to provide a liquid composition in which the precipitated non-sugar materials have been removed;
      (d) adding a lactase to the liquid composition thereby hydrolyzing lactose to produce D-galactose in a hydrolysate composition;
      (e) removing proteins by treating the hydrolysate composition with activated carbon for 4 hours to 6 hours at a temperature of 60° C. to 70° C.; and
      (f) removing ash, salts, or both from the deproteinized composition, thereby producing said purified D-galactose;
   (ii) collecting the purified D-galactose subsequent to said removing ash, salts, or both; and
   (iii) isomerizing the collected D-galactose to produce D-tagatose.

10. The method according to claim 9, wherein in step (b) the heat treatment is performed at a temperature between 40° C. and 90° C. and/or the pH adjustment comprises adjusting the pH of the whey permeate composition from 3 to 9.

11. The method according to claim 9, wherein the whey permeate composition is a byproduct obtained from production of whey protein isolates and comprises lactose, proteins, ash, and salts.

12. The method according to claim 9, wherein in step (f) the removing comprises removing the ash, salts, or both by electrodialysis from the deproteinized composition.

13. The method according to claim 9, wherein the hydrolyzing is performed at 35° C. to 39° C. for 50 hours to 60 hours.

* * * * *